US011266807B2

(12) United States Patent
Garcia Molina et al.

(10) Patent No.: US 11,266,807 B2
(45) Date of Patent: Mar. 8, 2022

(54) SYSTEM AND METHOD FOR DETERMINING WHETHER A SUBJECT IS LIKELY TO BE DISTURBED BY THERAPY LEVELS OF STIMULATION DURING SLEEP SESSIONS

(71) Applicant: KONINKLIJKE PHILIPS N.V., Eindhoven (NL)

(72) Inventors: Gary Nelson Garcia Molina, Madison, WI (US); Surya Subrahmanya Sreeram Vissapragada Venkata Satya, Monroeville, PA (US); Stefan Pfundtner, Eindhoven (NL); Tsvetomira Kirova Tsoneva, Eindhoven (NL); Anandi Mahadevan, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 285 days.

(21) Appl. No.: 16/472,621

(22) PCT Filed: Dec. 27, 2017

(86) PCT No.: PCT/EP2017/084594
§ 371 (c)(1),
(2) Date: Jun. 21, 2019

(87) PCT Pub. No.: WO2018/122226
PCT Pub. Date: Jul. 5, 2018

(65) Prior Publication Data
US 2021/0128867 A1 May 6, 2021

Related U.S. Application Data

(60) Provisional application No. 62/439,544, filed on Dec. 28, 2016.

(51) Int. Cl.
*A61M 21/02* (2006.01)
*A61B 5/00* (2006.01)
*A61M 21/00* (2006.01)

(52) U.S. Cl.
CPC .......... *A61M 21/02* (2013.01); *A61B 5/4836* (2013.01); *A61M 2021/0027* (2013.01);
(Continued)

(58) Field of Classification Search
CPC ............ A61M 21/00–02; A61B 5/4806–4815
See application file for complete search history.

(56) References Cited

U.S. PATENT DOCUMENTS 10,137,276 B2 11/2018 Garcia Molina et al.
10,183,142 B2 1/2019 Garcia Molina et al.
(Continued)

FOREIGN PATENT DOCUMENTS

WO WO-2014170781 A1 * 10/2014 ............ A61M 21/02
WO WO-2015049613 A1 * 4/2015 ........... A61B 5/4836
(Continued)

OTHER PUBLICATIONS

International Search Report and Written Opinion, International Application No. PCT/EP2017/084594, dated Mar. 29, 2018.
(Continued)

*Primary Examiner* — Thaddeus B Cox

(57) ABSTRACT

The present disclosure pertains to a system and method for determining whether a subject is likely to be disturbed by therapy levels of stimulation provided to the subject during sleep sessions. The present system is configured to automatically identify sensitive users using electroencephalogram (EEG) information from a reference sleep session with or without stimulation. For reference sleep sessions without stimulation, the alpha activity in detected deep sleep is used to predict whether the subject is likely to be disturbed by
(Continued)

therapy levels of stimulation. For reference sleep sessions with stimulation, the acute increase in EEG delta (e.g., 0.5-4 Hz) power and/or an arousability index are used to predict whether the subject is likely to be disturbed by therapy levels of stimulation.

18 Claims, 12 Drawing Sheets

(52) U.S. Cl.
CPC .............. *A61M 2021/0055* (2013.01); *A61M 2205/502* (2013.01); *A61M 2230/10* (2013.01)

(56) References Cited

U.S. PATENT DOCUMENTS

| | | |
|---|---|---|
| 10,220,183 B2 | 3/2019 | Garcia Molina et al. |
| 2013/0338446 A1* | 12/2013 | Van Vugt ............. A61B 5/6814 600/300 |
| 2016/0082222 A1* | 3/2016 | Garcia Molina ...... A61B 5/375 600/27 |
| 2016/0220783 A1* | 8/2016 | Garcia Molina .... A61B 5/4812 |
| 2016/0296164 A1 | 10/2016 | Garcia Molina et al. |
| 2016/0302718 A1 | 10/2016 | Laura Lapoint et al. |
| 2017/0304587 A1* | 10/2017 | Santostasi ............ A61B 5/4857 |
| 2018/0078734 A1 | 3/2018 | Pfundtner |

FOREIGN PATENT DOCUMENTS

| | | |
|---|---|---|
| WO | 2015118415 A1 | 8/2015 |
| WO | 2016087983 A1 | 6/2016 |

OTHER PUBLICATIONS

Neckelmann, D. et al., "Sleep Stages and EEG Power Spectrum in Relation to Acoustical Stimulus Arousal Threshold in the Rat", Sleep, 16(5):467-477, 1993.

H.-V. V Ngo, J. C. Claussen, J. Born, and M. Mölle, "Induction of slow oscillations by rhythmic acoustic stimulation.," J. Sleep Res., p. 10 pp, Aug. 2012.

H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.

M. Bellesi, B. A. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

G. Santostasi, R. Malkani, B. A. Riedner, M. Bellesi, G. Tononi, K. A. Paller, and P. C. Zee, "Phase-locked loop for precisely timed acoustic stimulation during sleep," J. Neurosci. Methods, pp. 1-14, 2015.

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

G. Tononi and C. Cirelli, "Sleep and the price of plasticity: from synaptic and cellular homeostasis to memory consolidation and integration.," Neuron, vol. 81, No. 1, pp. 12-34, Jan. 2014.

T. T. Dang-Vu, S. M. McKinney, O. M. Buxton, J. M. Solet, and J. M. Ellenbogen, "Spontaneous brain rhythms predict sleep stability in the face of noise.," Curr Biol., vol. 20, No. 15, pp. R626-R627, Aug. 2010.

P. Hauri and D. R. Hawkins, "Alpha-delta sleep," Electroencephalogr. Clin. Neurophysiol., vol. 34, No. 3, pp. 233-237, 1973.

\* cited by examiner

SYSTEM AND METHOD FOR DETERMINING WHETHER A SUBJECT IS LIKELY TO BE DISTURBED BY THERAPY LEVELS OF STIMULATION DURING SLEEP SESSIONS

CROSS-REFERENCE TO PRIOR APPLICATIONS

This application is the U.S. National Phase application under 35 U.S.C. § 371 of International Application Serial No. PCT/EP2017/084594, filed on 27 Dec. 2017, which claims the benefit of U.S. Application Ser. No. 62/439,544, filed on 28 Dec. 2016. These applications are hereby incorporated by reference herein.

BACKGROUND

1. Field

The present disclosure pertains to a system and method for determining whether a subject is likely to be disturbed by therapy levels of stimulation provided to the subject during sleep sessions.

2. Description of the Related Art

Systems for monitoring sleep are known. The restorative value of sleep can be increased by delivering appropriately timed auditory stimulation during deep sleep to enhance sleep slow waves. Typical systems do not automatically determine whether a subject is likely to be disturbed by therapy levels of stimulation provided to the subject during sleep sessions.

SUMMARY

Accordingly, one or more aspects of the present disclosure relate to a system configured to determine whether a subject is likely to be disturbed by therapy levels of stimulation provided to the subject during sleep sessions. The system comprises one or more stimulators configured to provide the stimulation to the subject during the sleep sessions, one or more sensors configured to generate output signals conveying information related to brain activity in the subject during the sleep sessions, and one or more hardware processors operatively communicating with the one or more stimulators and the one or more sensors. The one or more hardware processors are configured by machine-readable instructions to: (1) control the one or more stimulators to provide low intensity stimulation to the subject during a reference sleep session, the low intensity stimulation comprising stimulation that does not cause sleep disturbances in the subject during the reference sleep session; or (2) control the one or more stimulators to provide high intensity stimulation to the subject during the reference sleep session, the high intensity stimulation comprising stimulation that causes sleep disturbances in the subject during the reference sleep session. The one or more hardware processors are also configured to determine a brain activity parameter of the subject that corresponds to the low intensity stimulation or the high intensity stimulation based on the output signals during the reference sleep session, compare the brain activity parameter to a brain activity parameter threshold that indicates whether the subject is likely to be disturbed by the therapy levels of stimulation, and responsive to the brain activity parameter breaching the brain activity parameter threshold, determine that the subject is likely to be disturbed by the therapy levels of stimulation.

Yet another aspect of the present disclosure relates to a method for determining, with a determination system, whether a subject is likely to be disturbed by therapy levels of stimulation provided to the subject during sleep sessions. The system comprises one or more stimulators, one or more sensors, and one or more hardware processors. The method comprises providing, with the one or more stimulators, the stimulation to the subject during the sleep sessions; and generating, with the one or more sensors, output signals conveying information related to brain activity in the subject during the sleep sessions. The method also comprises (1) controlling, with the one or more processors, the one or more stimulators to provide low intensity stimulation to the subject during a reference sleep session, the low intensity stimulation comprising stimulation that does not cause sleep disturbances in the subject during the reference sleep session; or (2) controlling, with the one or more processors, the one or more stimulators to provide high intensity stimulation to the subject during the reference sleep session, the high intensity stimulation comprising stimulation that causes sleep disturbances in the subject during the reference sleep session. The method also comprises determining, with the one or more processors, a brain activity parameter of the subject that corresponds to the low intensity stimulation or the high intensity stimulation based on the output signals during the reference sleep session, comparing the brain activity parameter to a brain activity parameter threshold that indicates whether the subject is likely to be disturbed by the therapy levels of stimulation, and responsive to the brain activity parameter breaching the brain activity parameter threshold, determining that the subject is likely to be disturbed by the therapy levels of stimulation.

Still another aspect of present disclosure relates to a system for determining whether a subject is likely to be disturbed by therapy levels of stimulation provided to the subject during sleep sessions. The system comprises means for providing the stimulation to the subject during the sleep sessions and means for generating output signals conveying information related to brain activity in the subject during the sleep sessions. The system also comprises means for controlling the means for providing to provide low intensity stimulation to the subject during a reference sleep session, the low intensity stimulation comprising stimulation that does not cause sleep disturbances in the subject during the reference sleep session; or means for controlling the means for providing to provide high intensity stimulation to the subject during the reference sleep session, the high intensity stimulation comprising stimulation that causes sleep disturbances in the subject during the reference sleep session. The system also comprises means for determining a brain activity parameter of the subject that corresponds to the low intensity stimulation or the high intensity stimulation based on the output signals during the reference sleep session, comparing the brain activity parameter to a brain activity parameter threshold that indicates whether the subject is likely to be disturbed by the therapy levels of stimulation, and responsive to the brain activity parameter breaching the brain activity parameter threshold, determining that the subject is likely to be disturbed by the therapy levels of stimulation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
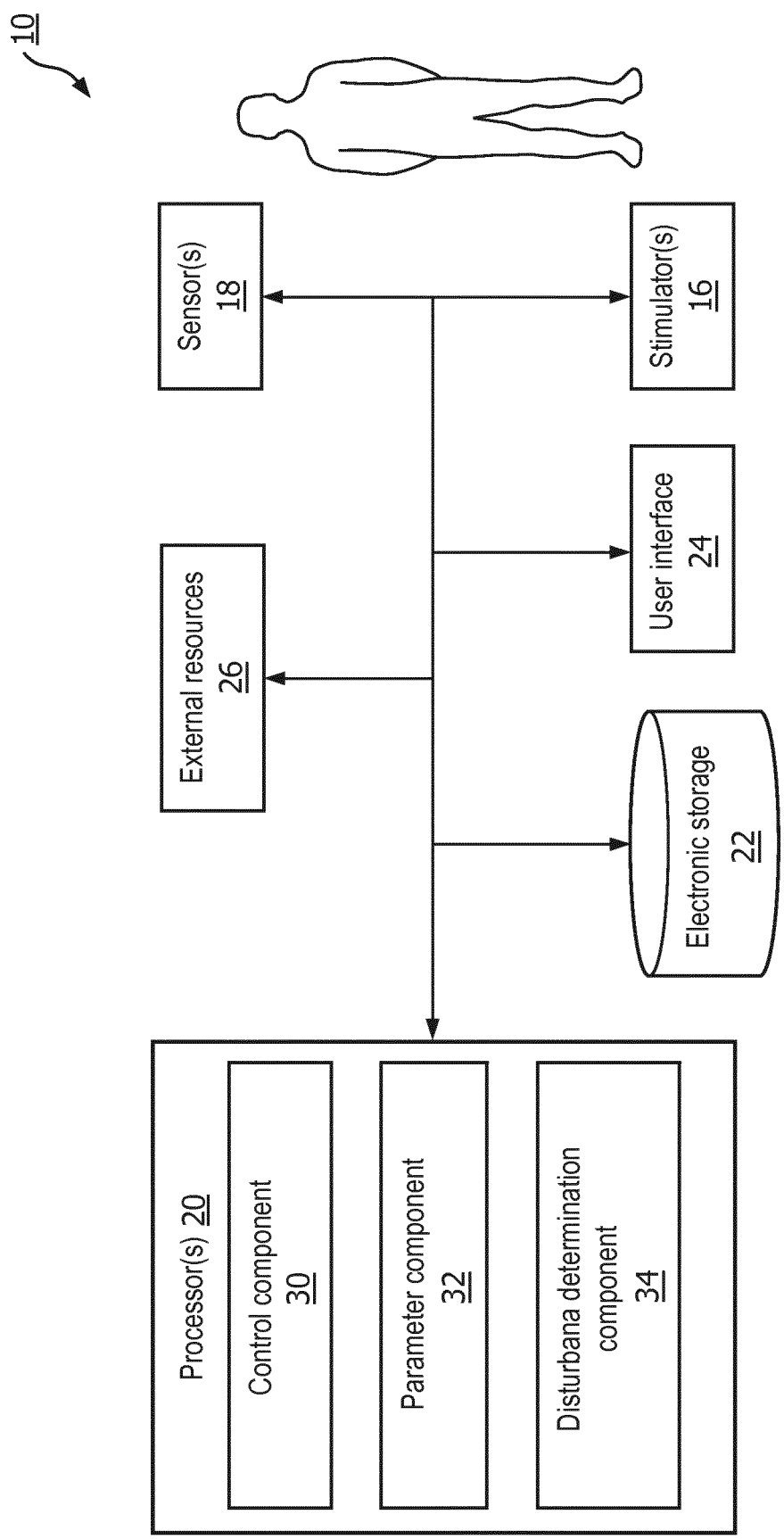
FIG. 1 illustrates a system for determining whether a subject is likely to be disturbed by therapy levels of stimulation provided to the subject during sleep sessions.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to determine whether a subject 12 is likely to be disturbed by therapy levels of stimulation provided to subject 12 during sleep sessions. Sleep slow waves can be enhanced through stimulation delivered during non-rapid eye movement (NREM) sleep. The enhancement of sleep slow-waves increases the restorative value of sleep. The stimulation that enhances sleep slow waves and/or increases the restorative value of sleep and/or other stimulation may be the therapy stimulation. System 10 is configured to delivered such therapy stimulation to subject 12 (e.g., controlled by control component 30 described below).

Figure 2:
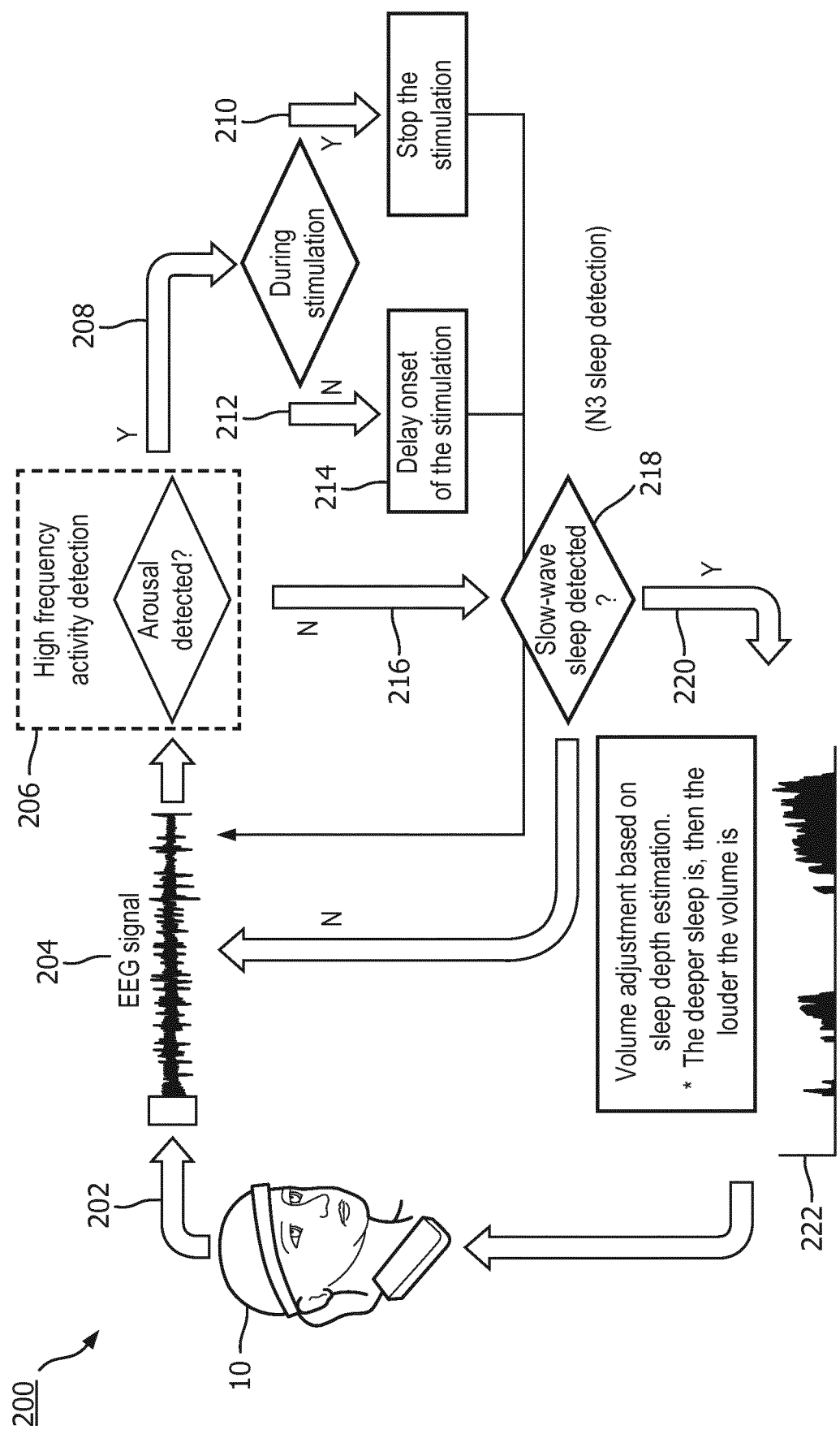
FIG. 2 is an example illustration of sleep therapy operations performed by the system.

An example illustration of sleep therapy operations 200 performed by system 10 (also shown in FIG. 1) is shown in FIG. 2. As shown in FIG. 2, electroencephalogram (EEG) electrodes generate 202 an EEG signal 204. The presence of EEG patterns (high power in the alpha 8-12 Hz and/or beta 15-30 Hz bands) indicative of (micro) arousals is evaluated 206 by system 10. If arousal-like activity is detected 208 in the EEG during stimulation, stimulation is controlled to stop 210. If the arousal-like activity is detected 212 outside the stimulation period, the onset of the next stimulation is delayed 214. If no arousal-like activity is detected 216, then system 10 attempts to detect 218 deep sleep based on the power in the slow wave activity band (0.5 to 4 Hz), the temporal density of detected slow-waves, and/or other information. Responsive to detection of sufficiently deep sleep 220, system 10 is configured such that auditory (as in the example shown in FIG. 2 but this is not intended to be limiting) stimulation is delivered 222. System 10 is configured such that the volume (for example) of the auditory (for example) stimulation is modulated by a real time EEG based estimation of sleep depth that considers the sum of power ratios: delta power/alpha power+delta power/beta power. Consequently, the deeper sleep is, the louder the volume of the stimulation becomes. In some embodiments, system 10 is configured such that therapy levels of stimulation comprise intensities, durations, etc., of stimulation provided to subject 12 during the operations described above.

Figure 3:
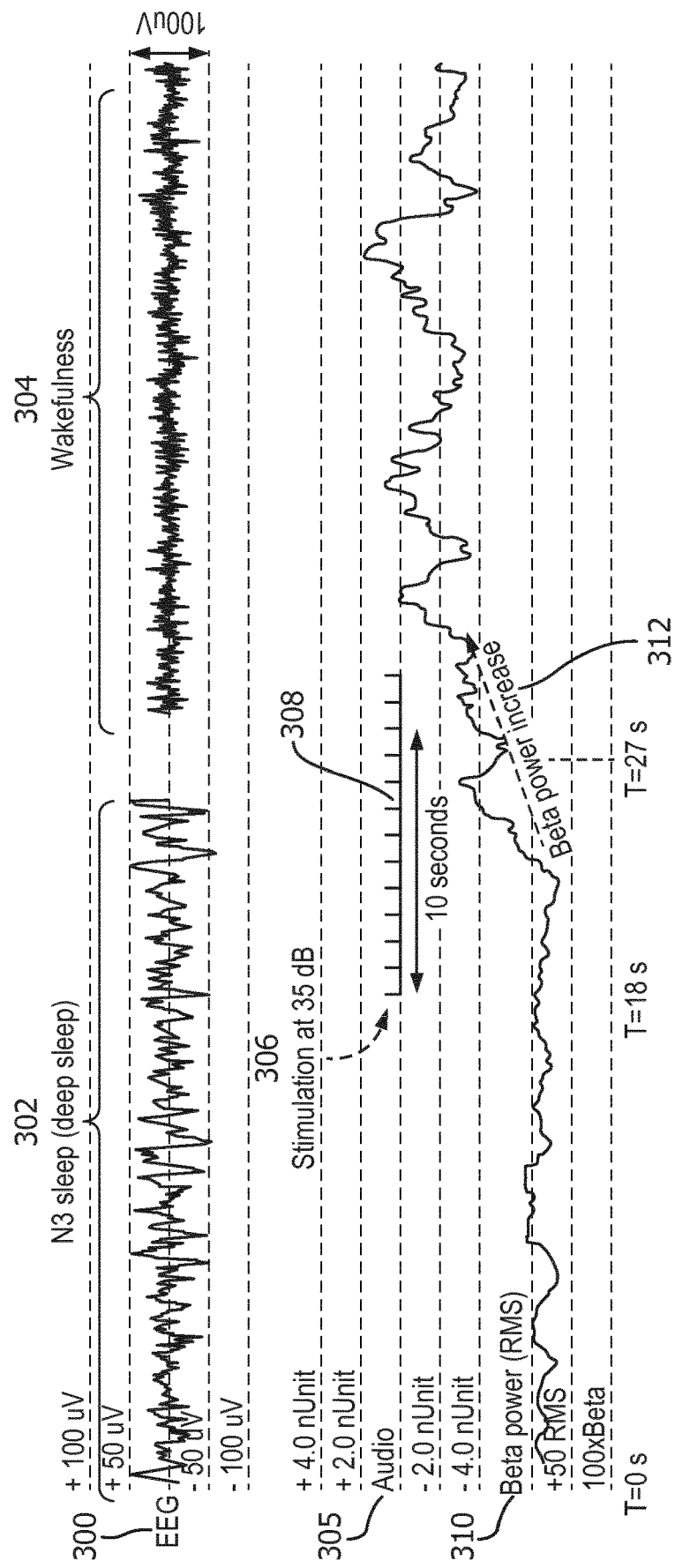
FIG. 3 illustrates sleep disturbance caused by therapy levels of stimulation.

A non-negligible proportion of users (e.g., about a third) are too sensitive (likely to be disturbed by therapy levels of stimulation) to even low intensity (e.g., volume) auditory and/or other stimulation to receive the therapy stimulation described above. For example, FIG. 3 illustrates sleep disturbance caused by therapy levels of stimulation. Disturbance due to stimulation at 35 dB is shown in FIG. 3 where the EEG signal 300 shows that the period 302 of deep sleep characterized by large slow oscillations (e.g., up to time T=27 seconds), transitions into wakefulness 304 (characterized by small fast oscillations) caused by the audio 305 (for example) stimulation 306 (e.g., starting at time T=18 seconds). The timing of individual stimulations 308 is illustrated in audio signal 305. The EEG power in the beta (e.g., from 15 to 30 Hz) band 310 is also shown. It can be observed that the beta power, in root mean square (RMS) units, increases 312 at the transition from deep sleep to wakefulness. Typically, the categorization of a user as sensitive (likely to be disturbed by therapy levels of stimulation) typically happens only after sleep data after a sleep session with stimulation becomes available.

Returning to FIG. 1, system 10 is configured to use thresholds on the power in the alpha/beta bands, on a quantity of micro arousals, and/or on other parameters to detect the arousal activity leading to wakefulness during the therapy stimulation described above. In typical systems, such thresholds are set such that stimulation stops before an arousal transitions into wakefulness. However, in sensitive users with typical systems, additional intensity (e.g., volume) adjustment operations (e.g., waiting a longer time after deep sleep detection before stimulation begins, delivering the stimulation at a given phase of a detected slow-wave, and/or other operations) to prevent sleep disturbance during typical sleep therapy are necessary. System 10 is configured such that these additional adjustment operations are not necessary.

System 10 identifies these sensitive users before they experience potentially sleep disturbing stimulation based on information from a reference sleep session (e.g., a sleep night, a nap, a sleep cycle, etc.) without stimulation, or with stimulation at low and/or high intensity (e.g., volume) as described herein. System 10 determines the likelihood that a given user (e.g., subject 12) is sensitive to auditory and/or other stimulation based on such information.

Figure 4:
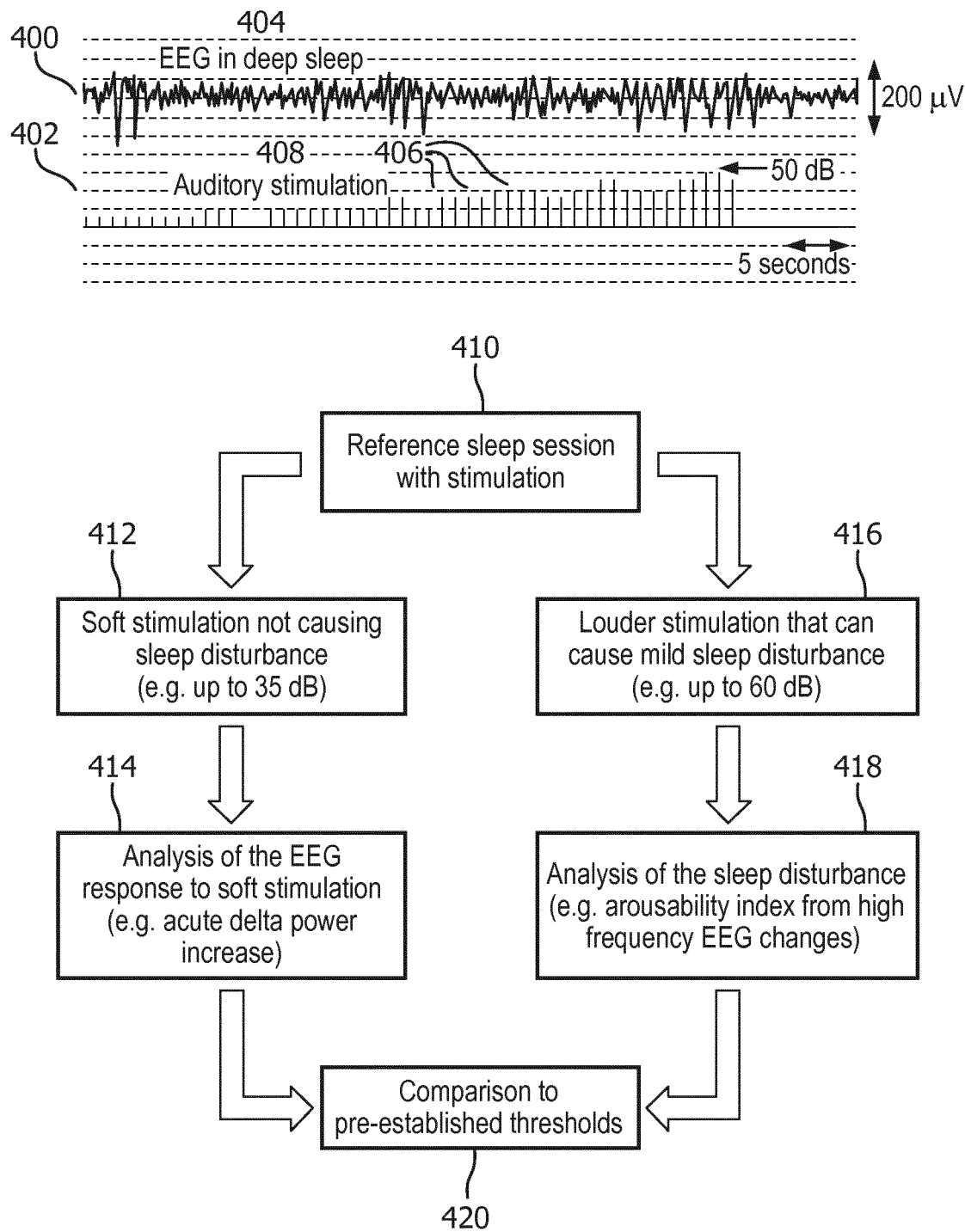
FIG. 4 illustrates an example embodiment of the system wherein stimulation is delivered during a reference sleep session.

FIG. 4 illustrates an example embodiment of system 10 (shown in FIG. 1 and further described below) wherein stimulation is delivered during a reference sleep session. Signals 400 and 402 show the EEG signal 404 for deep sleep and corresponding instances 406 of auditory (in this example) stimulation 408. In this example, system 10 is configured such that, during the reference sleep session with stimulation 410: (A) the stimulation is delivered at a low intensity/soft volume (e.g., up to about 35 dB) 412 so that it does not cause sleep disturbance, but influences the brain activity of subject 12 (FIG. 1) so the effect can be observed in the EEG signal (e.g., the increase in delta power, 0.5 to 4 Hz, as described below) 414; and/or (B) the stimulation is delivered at a high intensity/louder volume (e.g., up to about 60 dB) 416 such that it may cause disturbance to facilitate determination 418 of the sensitivity of subject 12 to stimulation. Various thresholds (e.g., as described below) are used to determine 420 whether subject 12 and/or other users are likely to be disturbed by therapy levels of stimulation.

Figure 5:
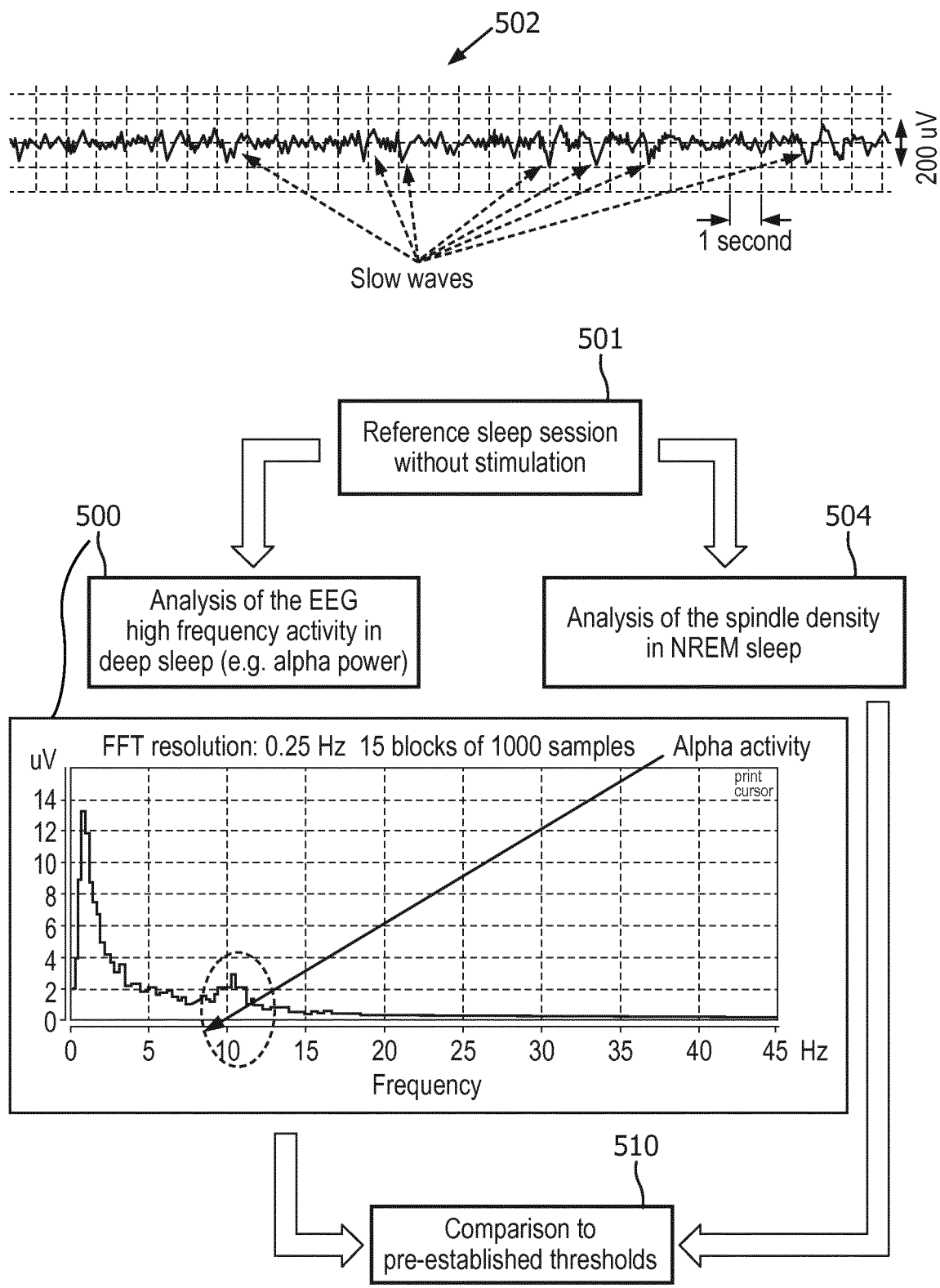
FIG. 5 illustrates an example embodiment of the system wherein no stimulation is delivered during a reference sleep session.

FIG. 5 illustrates an example embodiment of system 10 (shown in FIG. 1 and further described below) wherein no stimulation is delivered during a reference sleep session 501. As shown in FIG. 5, system 10 is configured to analyze the spectral properties 500 of the EEG 502 during automatically detected NREM sleep (e.g., N3 sleep as described further below). In embodiments where no stimulation is delivered during a sleep session, the EEG in deep sleep for sensitive users (e.g., subject 12) exhibits spectral activity in the alpha (8-12 Hz) and/or beta (15-30 Hz) bands that is higher than normal (e.g., compared to that of age and/or gender matched users). In addition to the spectral properties in the alpha and beta bands, system 10 may be configured such that the density of spindles for detected NREM sleep is used 504 to determine whether subject 12 is likely to be disturbed by therapy levels of stimulation. Spindles may be associated with robustness of sleep against disturbances such as noise, for example. Like reference sleep sessions where stimulation is provided to subject 12 (e.g., as described related to FIG. 4 above), various thresholds for the spectral activity, the spindles, and/or other parameters are used to determine 510 whether subject 12 and/or other users are likely to be disturbed by therapy levels of stimulation.

Returning to FIG. 1, in some embodiments, system 10 includes one or more of a stimulator 16, a sensor 18, a processor 20, electronic storage 22, a user interface 24, external resources 26, and/or other components.

Stimulator 16 is configured to provide electric, magnetic, sensory, and/or other stimulation to subject 12. Stimulator 16 is configured to provide electric, magnetic, sensory, and/or other stimulation to subject 12 prior to a sleep session, during a sleep session, and/or at other times. For example, stimulator 16 may be configured to provide stimuli to subject 12 during a sleep session to facilitate a transition to a deeper stage of sleep, a lighter stage of sleep, maintain sleep in a specific stage, and/or for other purposes. In some embodiments, stimulator 16 may be configured such that facilitating a transition between deeper sleep stages and lighter sleep stages includes decreasing sleep slow waves in subject 12, and facilitating a transition between lighter sleep stages and deeper sleep stages includes increasing sleep slow waves.

Stimulator 16 is configured to facilitate transitions between sleep stages and/or maintain sleep in a specific stage through non-invasive brain stimulation and/or other methods. Stimulator 16 may be configured to facilitate transitions between sleep stages and/or maintain sleep in a specific stage through non-invasive brain stimulation using electric, magnetic, and/or sensory stimuli. The electric, magnetic, and/or sensory stimulation may include auditory stimulation, visual stimulation, somatosensory stimulation, electrical stimulation, magnetic stimulation, a combination of different types of stimulation, and/or other stimulation. The electric, magnetic, and/or sensory stimuli include odors, sounds, visual stimulation, touches, tastes, somatosensory stimulation, haptic, electrical, magnetic, and/or other stimuli. For example, acoustic tones may be provided to subject 12 to facilitate transitions between sleep stages and/or maintain sleep in a specific stage. Examples of stimulator 16 may include one or more of a sound generator, a speaker, a music player, a tone generator, one or more electrodes on the scalp of subject 12, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, stimulator 16 is configured to adjust the intensity, timing, and/or other parameters of the stimulation provided to subject 12.

Sensor 18 is configured to generate output signals conveying information related to brain activity, activity of the central nervous system, activity of the peripheral nervous system, and/or other activity in subject 12. In some embodiments, the information related to brain activity includes the information related to the central nervous system, the information related to the activity of the peripheral nervous system, and/or other information. In some embodiments, sensor 18 is configured to generate output signals conveying information related to slow wave activity in subject 12. In some embodiments, the information related to brain activity, activity of the central nervous system, activity of the peripheral nervous system, and/or other activity in subject 12 is the information related to slow wave activity. In some embodiments, sensor 18 is configured to generate output signals conveying information related to stimulation provided to subject 12 during sleep sessions.

In some embodiments, the slow wave activity of subject 12 may correspond to a sleep stage of subject 12. The sleep stage of subject 12 may be associated with rapid eye movement (REM) sleep, NREM sleep, and/or other sleep. The sleep stage of subject 12 may be one or more of NREM stage N1, stage N2, stage N3, or stage N4 sleep, REM sleep, and/or other sleep stages. In some embodiments, NREM stage 3 and/or 4 may be slow wave (e.g., deep) sleep. Sensor 18 may comprise one or more sensors that measure such parameters directly. For example, sensor 18 may include EEG electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may comprise a heart rate sensor that generates an output based on a heart rate of subject 12 (e.g., sensor 18 may be a heart rate sensor than can be located on the chest of subject 12, and/or be configured as a bracelet on a wrist of subject 12, and/or be located on another limb of subject 12), movement of subject 12 (e.g., sensor 18 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, the one or more sensors comprise one or more of the EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to subject 12, and/or other sensors. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a control component 30, a parameter component 32, a disturbance determination component 34, and/or other components. Processor 20 may be configured to execute components 30, 32, and/or 34 by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, and/or 34 may be located remotely from the other components. The description of the functionality provided by the different components 30, 32, and/or 34 described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Control component 30 is configured to control one or more stimulators 16 to provide stimulation to subject 12 during sleep sessions. In some embodiments, the one or more stimulators 16 are controlled to provide stimulation according to a predetermined therapy regime (e.g., as shown in FIG. 2 described above). Sleep slow waves can be enhanced through (e.g. peripheral auditory, magnetic, electrical, and/or other) stimulation delivered in NREM sleep. Control component 30 monitors the brain activity of subject 12 based on the output signals of sensors 18 (e.g., based on an EEG) and/or other information during sleep sessions and controls the delivery of stimulation (e.g., auditory and/or other stimulation) by stimulator 16 to control slow wave activity in subject 12. In some embodiments, control component 30 (and/or or more of the other processor components described below) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

In some embodiments, control component 30 is configured to control stimulator 16, during a reference sleep session, to provide low intensity stimulation, provide high intensity stimulation, and/or not provide any stimulation at all to subject 12. In some embodiments, stimulator 16 is controlled to provide the low intensity stimulation and the high intensity stimulation at different times during the same reference sleep session (e.g., as shown in FIG. 4 described above). In some embodiments, control component 30 is configured such that a reference sleep session comprises a night of sleep, a nap, a sleep cycle, and/or other sleep sessions. In some embodiments, a reference sleep session may be pre-planned by subject 12 and/or other users, and/or have other characteristics. In some embodiments, a reference sleep session comprises any sleep session where control component 30 controls stimulator 16 to provide the low intensity stimulation, the high intensity stimulation, and/or not to provide the stimulation to subject 12.

In some embodiments, control component 30 is configured to facilitate user (e.g., subject 12 and/or other users such as doctors, nurses, caregivers, family members, researchers, etc.) direction of reference sleep sessions (e.g., when such sleep sessions should occur and/or which type of and/or lack of stimulation should be used) via entry and/or selection of information using user interface 24 and/or other components of system 10. In some embodiments, control component 30 is configured to facilitate (e.g., subjective) input from the user regarding sensitivity to external noise and corresponding sleep disturbance. In some embodiments, control component 30 is configured such that results from auditory tests may also be used to decide on the nature (e.g., more intense/less intense) of the stimulation (if any) that needs to be applied.

In some embodiments, (e.g., responsive to subject 12 and/or other users specifying that system 10 should provide low intensity stimulation to subject 12 during a reference sleep session), control component 30 is configured such that the low intensity stimulation comprises stimulation that does not cause sleep disturbances in subject 12 during the reference sleep session. In some embodiments, the low intensity stimulation comprises stimulation that is high enough to elicit an EEG response but sufficiently low so that the stimulation does not disturb sleep. In some embodiments, the low intensity stimulation comprises tones with about a 30 to about a 40 decibel volume and/or other volumes. In some embodiments, the low intensity stimulation comprises up to five tone blocks and/or other blocks. In some embodiments, the low intensity stimulation comprises a randomized inter tone interval in about a 5 to about a 30 second range and/or other ranges. This is not intended to be limiting. For example, in a noisier environment, the low intensity stimulation may be more intense than the example low intensity stimulation described above.

Figure 6:
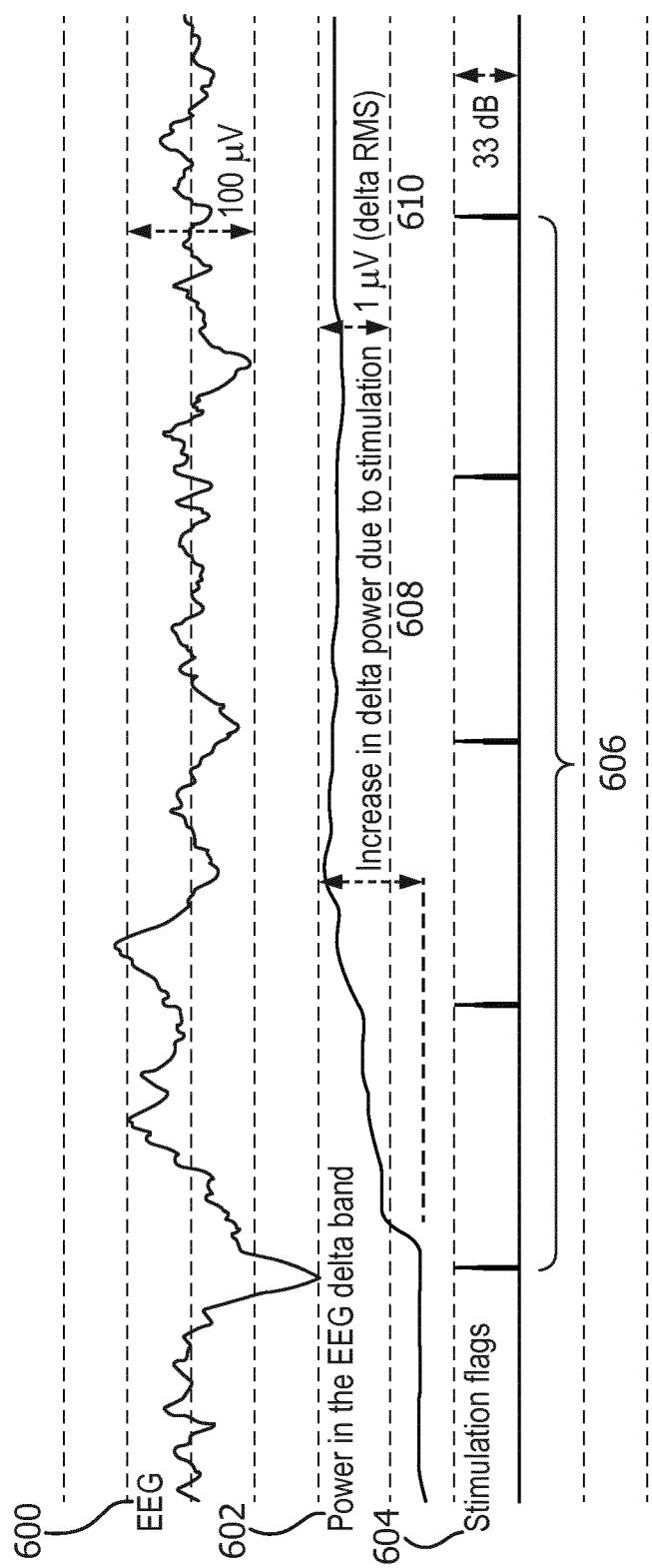
FIG. 6 illustrates an example of low intensity stimulation that is high enough to elicit an EEG response but sufficiently low so that the stimulation does not disturb sleep.

An example of low intensity stimulation that is high enough to elicit an EEG response but sufficiently low so that the stimulation does not disturb sleep is illustrated in FIG. 6. FIG. 6 illustrates an EEG signal 600, power in the EEG delta band 602 and stimulation flags 604. Stimulation flags 604 indicate the timing and the intensity (e.g., 33 dB) of auditory stimulation provided to subject 12 (FIG. 1). As shown in FIG. 6, the auditory stimulation occurred in a five tone block 606. Power in EEG delta band 602 increased 608 by about 1 µV (delta RMS) 610 as a result of the low intensity stimulation.

In low intensity stimulation embodiments, control component 30 may be configured such that multiple blocks 606 of stimulation comprising five (or less for example) tones (for example) can be delivered via stimulator 16 (FIG. 1) to determine (e.g., via parameter component 32 and/or other components described below) an EEG response that reflects the brain response of subject 12 (FIG. 1) to stimulation. Control component 30 may be configured such that the inter block interval duration is randomized in the approximately 5 to approximately 30 second range. In some embodiments, parameter component 32 (described below) is configured such that the EEG response to the stimulation is determined based on the instantaneous increase in the EEG delta (e.g., 0.5 to 4 Hz) power. The example in FIG. 6 shows that the delta power increases 608 by more than 1 microvolt from the moment the stimulation at 33 dB (indicated by stimulation flags 604) begins. In some embodiments, the increase in delta power is characterized as a percentage taking as a reference the two second (in this example) long period prior to the stimulation onset (which is referred to as time=0 in FIG. 6).

Figure 7:
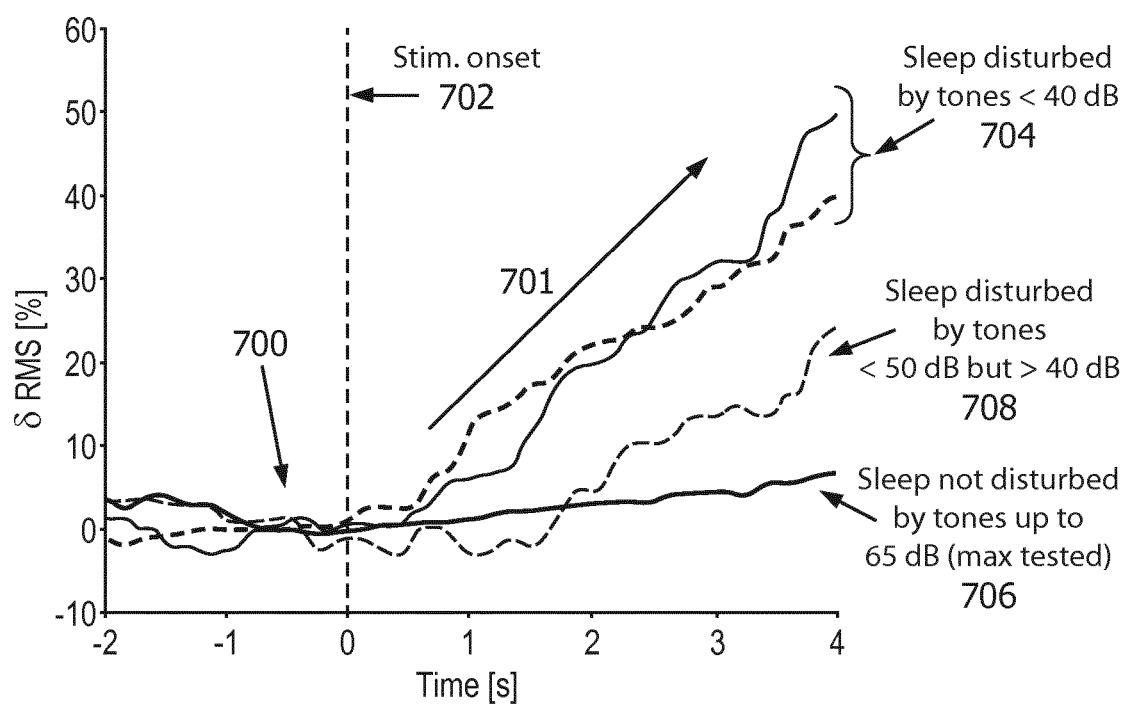
FIG. 7 illustrates example experimental results determined using the system with system providing the low intensity stimulation.

Example experimental results determined using system 10 with system 10 providing the low intensity stimulation are shown in FIG. 7. The example experimental results were determined using system 10 based on five subjects whose sensitivity to stimulation was known. As shown in FIG. 7, the delta increase curves 700 show that the delta power increase 701 in response to soft (e.g., <35 dB) and short (e.g., 4 tones) stimulation 704 (after stimulation onset 702) is higher for users whose sleep disturbed by softer tones. For example, the delta increase for users whose sleep is disturbed by 40 dB tones (stimulation 704) reaches a value that is higher than 30% (e.g., a 30% increase 701) after three seconds from stimulation onset 702. In addition, for a user whose sleep is not disturbed with tones up to 65 dB (stimulation 706), the delta increase barely reaches 10% (e.g., a 10% increase 701) even after four seconds from stimulation onset 702. Stimulation 708 produces a response between that of stimulation 704 and stimulation 706. Thus setting a threshold on the delta increase of, for example, 20% (e.g., by disturbance determination component 34 described below) facilitates identification of users (e.g., subject 12) that are likely to be disturbed by therapy levels of stimulation. In should be noted that while in this example the power in the delta band was used, it is possible that a (time-frequency) analysis of the EEG response to soft and/or short auditory stimulation reveals that other frequency bands may also and/or instead be used to characterize sensitivity to stimulation. In addition, the description of the 20% increase threshold on the delta power is not intended to be limiting. Other thresholds are contemplated.

Returning to FIG. 1, in some embodiments, (e.g., responsive to subject 12 and/or other users specifying that system 10 should provide high intensity stimulation to subject 12 during a reference sleep session), control component 30 is configured such that the high intensity stimulation comprises stimulation that causes sleep disturbances in the subject during the reference sleep session. In some embodiments, the extent of caused sleep disturbances are determined (e.g., by parameter component 32 and/or disturbance determination component 34 described below) based on an increase in detected micro and/or other arousals (e.g., characterized by increases in beta RMS above a pre-specified threshold). The micro and/or other arousals are used to determine whether subjects (e.g., subject 12) are sensitive (e.g., likely to be disturbed by therapy levels of stimulation). This is described further below.

Parameter component 32 is configured to determine one or more brain activity parameters for subject 12. The one or more brain activity parameters are determined based on the output signals and/or other information. In some embodiments, determining one or more brain activity parameters may include generating and/or monitoring an EEG during a sleep session of subject 12. The EEG may be displayed, for example, by user interface 24. In some embodiments, parameter component 32 is configured such that the one or more brain activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 2 Hz), also known as sleep slow waves, with peak-to-peak amplitudes greater than about 75 uV for sleep stage N3 and/or N4; presence of light sleep and/or arousals, and/or other characteristics. In some embodiments, light sleep may be characterized by the fact that the alpha activity (e.g., EEG power in the 8-12 Hz band) is no longer present and slow wave activity is not present. In addition, spindle activity (EEG power in the 11 to 16 Hz band) may be high. Deep sleep may be characterized by the fact that delta activity (e.g., EEG power in the 0.5 to 4 Hz band) is dominant. For example, in some embodiments, parameter component 32 is configured to determine a change in an EEG delta power level caused by the low intensity stimulation, a quantity of micro arousals in subject 12, an EEG alpha power level, and/or other parameters. In some embodiments, the quantity of micro arousals comprises a ratio of a quantity of micro arousals caused by the high intensity stimulation to a quantity of spontaneous micro arousals.

In some embodiments, parameter component 32 is configured to determine stimulation fragmentation parameters for stimulation provided to subject 12. In some embodiments, the stimulation fragmentation parameters include stimulation block lengths, maximum and/or minimum stimulation volumes, and/or other stimulation fragmentation parameters. In some embodiments, the stimulation fragmentation parameters are determined based on the output signals from sensor 18, the stimulation provided to subject 12, and/or other information.

In some embodiments, parameter component 32 is configured to determine the one or more brain activity parameters, the stimulation fragmentation parameters, and/or other parameters at predetermined times (e.g., intervals), substantially continuously, and/or at other times. In some embodiments, brain activity parameters may be determined based on the EEG signals, electrocardiogram (ECG) signals, actigraphy signals, body temperature signals, galvanic skin response (GSR) signals, and/or other information related to the brain, the central and/or peripheral nervous systems of subject 12, and/or other biological systems of subject 12.

Disturbance determination component 34 is configured to determine whether subject 12 is likely to be disturbed by therapy levels of stimulation. In some embodiments, determining whether subject 12 is likely to be disturbed by therapy levels of stimulation comprises obtaining and/or determining threshold levels for the one or more determined brain activity parameters that indicate whether the subject is likely to be disturbed by therapy levels of stimulation. Obtaining and/or determining threshold levels may include determining threshold levels based on information from prior sleep sessions of subject 12, facilitating entry and/or selection of threshold levels from subject 12 and/or other users (e.g., doctors, nurses, caregivers, family members, researchers, etc.) via user interface 24, receiving electronically transmitted threshold levels from one or more sources included in external resources 26, and/or other obtaining and/or determining. In some embodiments, the threshold levels are determined based on age and/or gender matched information (e.g., from external resources 26) for subject 12.

Disturbance determination component 34 is configured to compare one or more of the determined brain activity parameters to corresponding threshold levels for the brain activity parameter(s). In some embodiments, the comparison comprises determining whether a parameter breaches a corresponding threshold level. Breaching may comprising increasing to a level above the threshold level, decreasing to a level below the threshold level, matching the threshold level, and/or other breaching. Responsive to the brain activity parameter breaching the brain activity parameter threshold, disturbance determination component 34 is configured to determine that subject 12 is likely to be disturbed by the therapy levels of stimulation.

For example, in some embodiments, responsive to control component 30 controlling stimulator 16 to provide the low intensity stimulation during a reference sleep session and/or during a portion of a reference sleep session, parameter component 32 is configured such that the brain activity parameter comprises a change in an EEG delta power level caused by the low intensity stimulation. In such embodiments, disturbance determination component 34 is configured such that the threshold is a threshold level for the change in the delta power that indicates whether subject 12 is likely to be disturbed by the therapy levels of stimulation. For example, in the embodiment described above related to FIG. 7, a threshold on the delta power increase of, for example, 20% facilitates identification of users (e.g., subject 12) that are likely to be disturbed by therapy levels of stimulation.

As another example, in some embodiments, responsive to control component 30 controlling stimulator 16 to provide the high intensity stimulation during a reference sleep session and/or a portion of a reference sleep session, parameter component 32 is configured such that the brain activity parameter comprises a quantity of micro arousals in subject 12 during high intensity stimulation. In such embodiments, disturbance determination component 34 is configured such that the threshold is a threshold quantity of micro arousals that indicates whether subject 12 is likely to be disturbed by the therapy levels of stimulation. In some embodiments, the quantity of micro arousals comprises a ratio of a quantity of micro arousals caused by the high intensity stimulation to a quantity of spontaneous micro arousals, and the threshold is a threshold ratio for the micro arousals caused by the high intensity stimulation and the spontaneous arousals. In some embodiments, disturbance determination component 34 is configured to determine whether subject 12 is likely to be disturbed by therapy levels of stimulation based on a proximity (in time) of one or more micro arousals to corresponding instances of stimulation.

Figure 8:
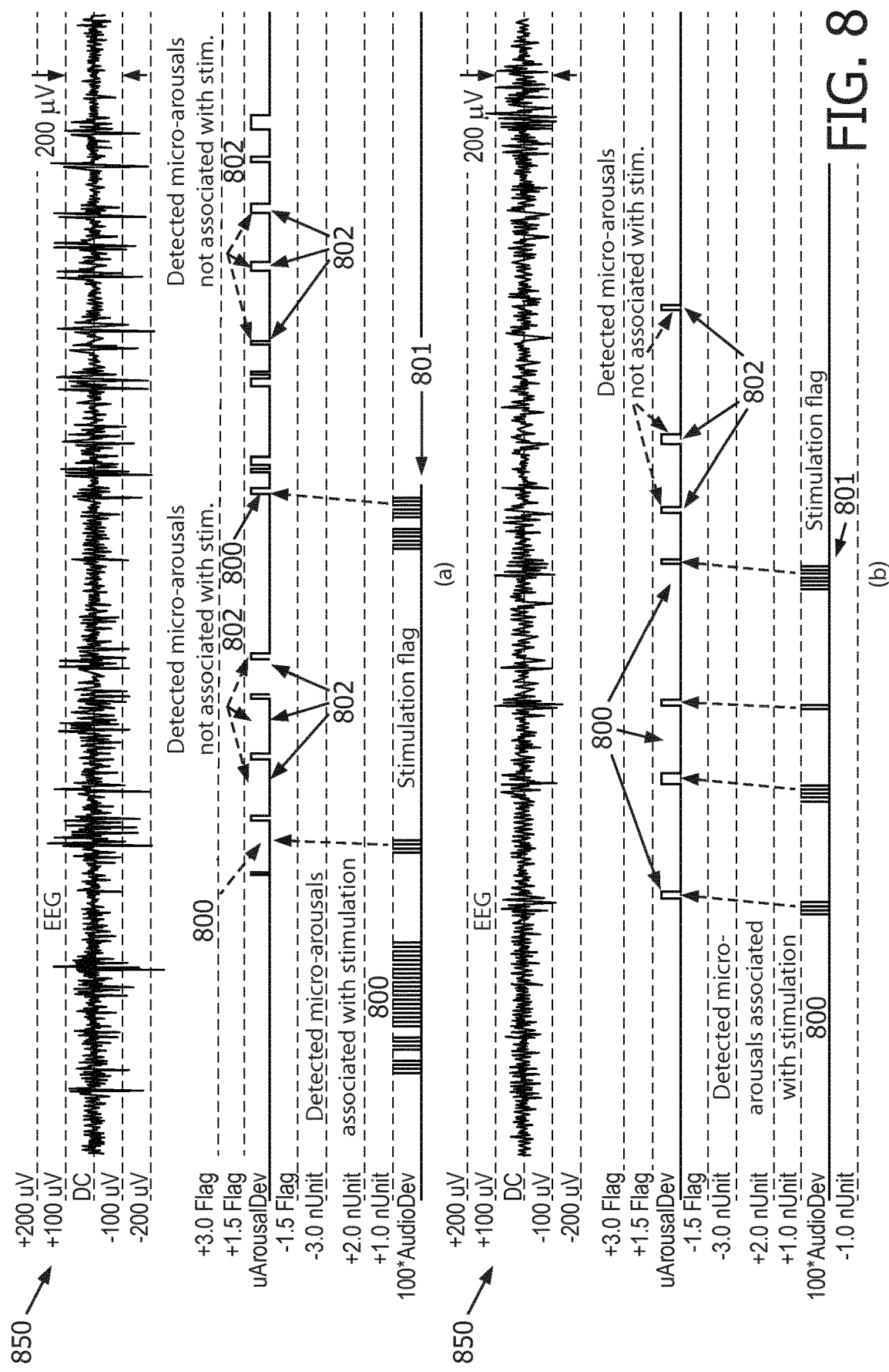
FIG. 8 illustrates micro arousals which are automatically detected using a threshold on the EEG power in the 15-30 Hz band and/or a threshold on the EEG power in the 8-12 Hz frequency band caused by high intensity stimulation and spontaneous micro arousals.

By way of a non-limiting example, FIG. 8 illustrates micro arousals 800 caused by high intensity stimulation 801 and spontaneous micro arousals 802. As shown in FIG. 8, the ratio of detected (based on EEG 850) micro arousals 800 caused by the stimulation 801 to the spontaneous micro arousals 802 is higher for subjects that are sensitive (likely to be disturbed by therapy levels of stimulation) to the stimulation (FIG. 8(b)) compared to subjects that are not sensitive (unlikely to be disturbed by therapy levels of stimulation) to the stimulation (FIG. 8(a)). In some embodiments, threshold levels depend on the duration of the stimulation. For example, reference levels for such thresholds may include, for a sensitive subject, arousals caused by the stimulation/duration of the stimulation=⅕ (e.g., a sensitive subject will have 1 caused arousal per 5 tones). For a non sensitive subject, <1/60 (e.g., less than 1 detected arousal per 60 seconds of stimulation). For spontaneous arousals, <1 arousal/60 seconds of detected N3 sleep. Other threshold levels are contemplated.

Figure 9:
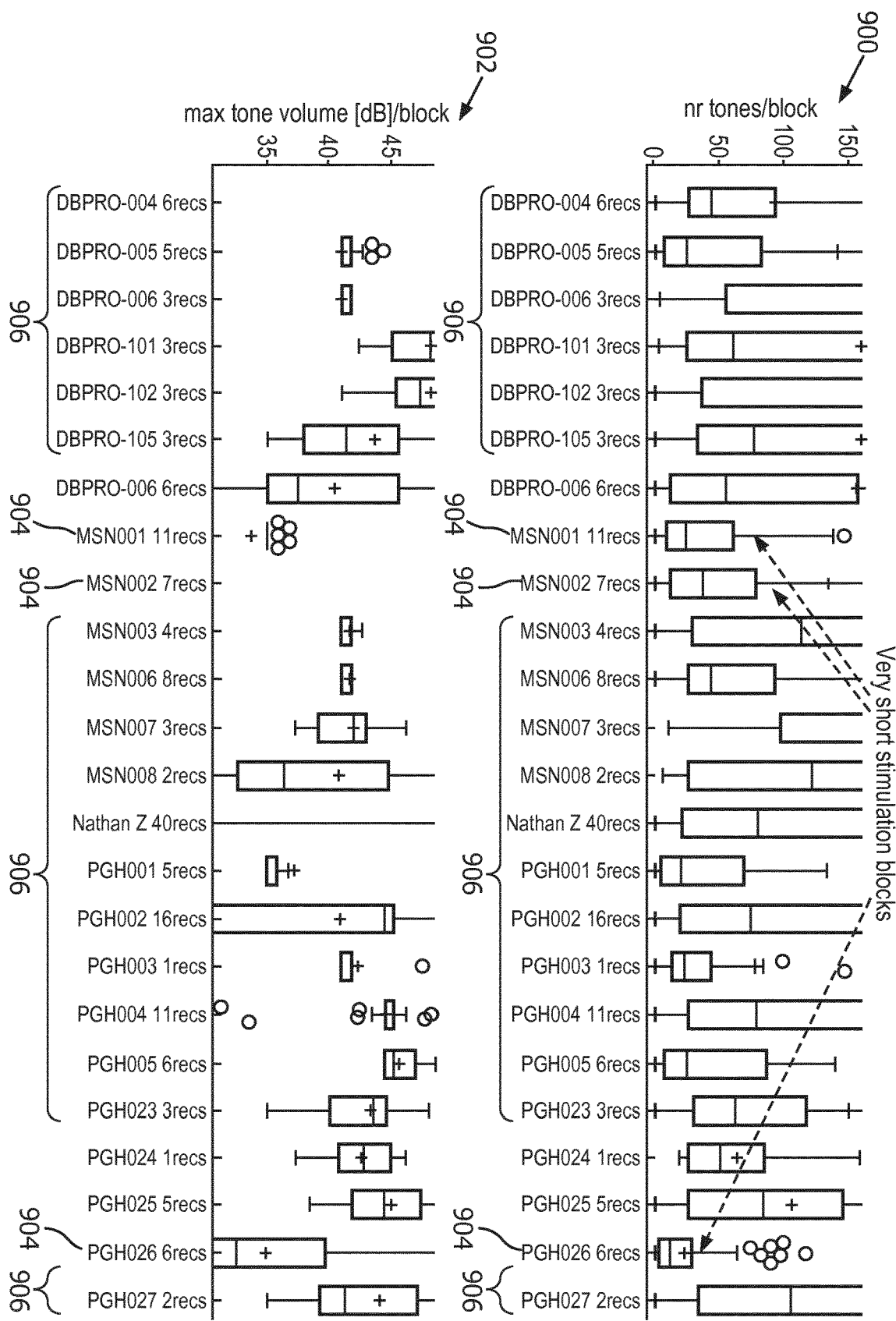
FIG. 9 illustrates that subjects who are disturbed by stimulation have shorter stimulation blocks during normal therapy sleep sessions and/or in reference sleep sessions, and are provided a lower maximum intensity of stimulation relative to subjects less likely to be disturbed by therapy levels of stimulation.

Returning to FIG. 1, in some embodiments, disturbance determination component 34 is configured such that stimulation fragmentation is used to determine the sensitivity (the likelihood that subject 12 will be disturbed by therapy levels of stimulation) of subject 12. For example, subjects (e.g., subject 12) who are disturbed by stimulation have shorter stimulation blocks during normal therapy sleep sessions (e.g., as shown in FIG. 2) and/or in reference sleep sessions, and are provided (e.g., by stimulator 16 controlled by control component 30) a lower maximum intensity (e.g., volume) of stimulation relative to subjects less likely to be disturbed by therapy levels of stimulation. This is illustrated in FIG. 9. As shown in FIG. 9, length of stimulation blocks 900 and maximum volume of stimulation 902 are generally lower for sensitive subjects 904 (e.g., as indicated by the arrows) relative to subjects 906 that are not sensitive (unlikely to be disturbed by therapy levels of stimulation) to the stimulation.

Returning to FIG. 1, in some embodiments, responsive to control component 30 controlling stimulator 16 not to provide stimulation during a reference sleep session and/or during a portion of a reference sleep session, parameter component 32 is configured such that the brain activity parameter comprises an EEG alpha power level during non-stimulation. In such embodiments, disturbance determination component 34 is configured such that the threshold is a threshold level for the alpha power that indicates whether the subject is likely to be disturbed by the therapy levels of stimulation. Subjects (e.g., subject 12) who are sensitive (likely to be disturbed by therapy levels) to stimulation show a higher (relative to non-sensitive subjects) level of alpha (8 to 12 Hz) activity in their deep sleep (e.g., N3 sleep) EEG. For example, in such embodiments, one possible threshold level (there are others) includes a threshold on the average RMS (root mean square) power in the alpha band during detected N3 sleep of 1.3.

Figure 10:
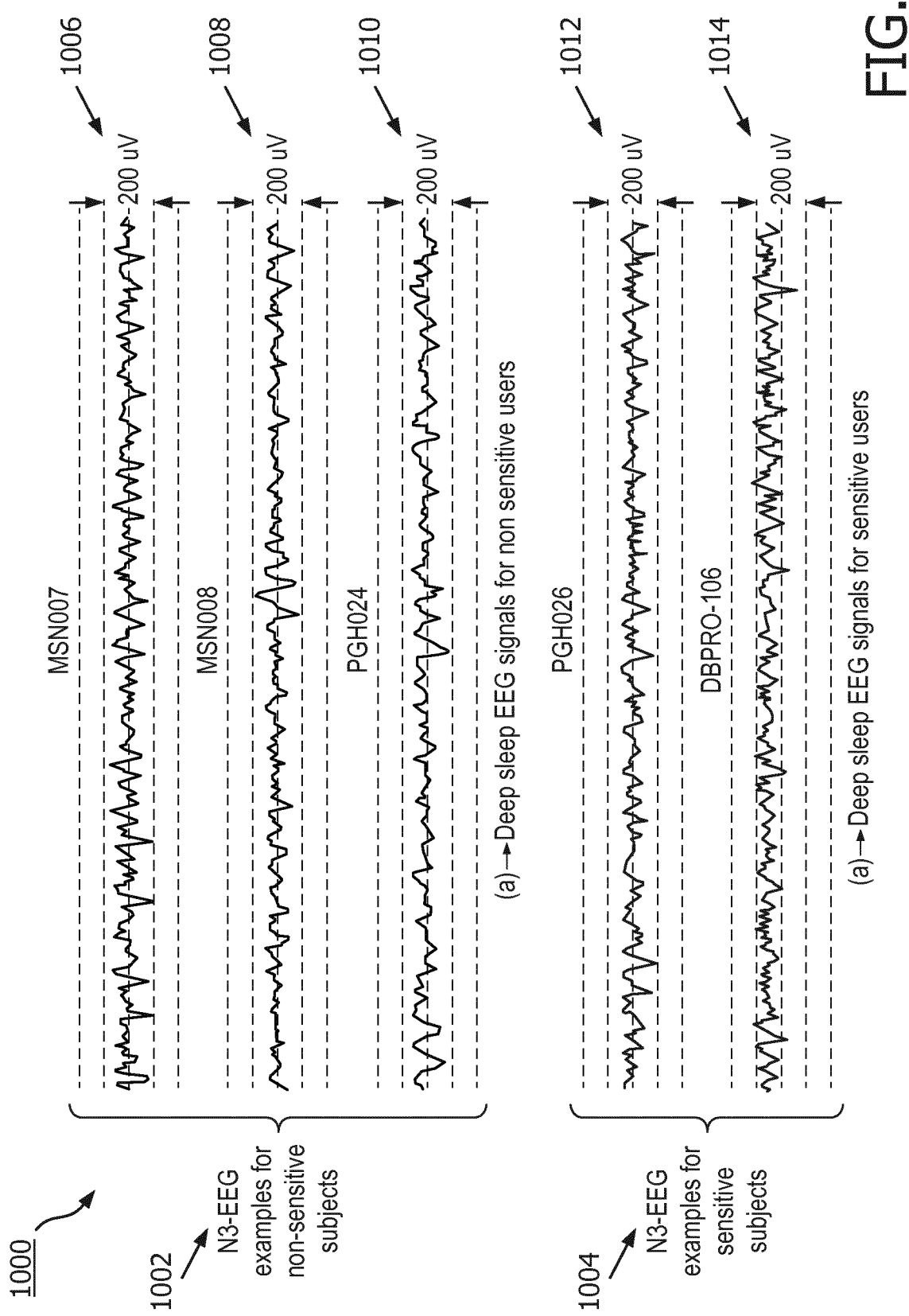
FIG. 10 illustrates alpha activity differences in deep sleep electroencephalogram examples for non-sensitive and sensitive subjects.

This is illustrated in FIG. 10. FIG. 10 illustrates alpha activity differences in N3 EEG examples 1000 for non-sensitive 1002 and sensitive 1004 subjects 1006 (non-sensitive), 1008 (non-sensitive), 1010 (non-sensitive), 1012 (sensitive), and 1014 (sensitive). As shown in FIG. 10, high frequency (e.g., alpha) EEG activity is more salient for subjects 1012 and 1014. For example, if, for the power in the alpha (8-12 Hz) band during N3 sleep, the power (in RMS values) exceeds 1.3, it can be considered as alpha presence in deep sleep. However, it should be noted that these subjects do not necessarily exhibit the alpha intrusion phenomenon in deep sleep (also known as alpha/delta sleep which is indicative of certain pathologies such as chronic pain or unrestful sleep).

Figure 11:
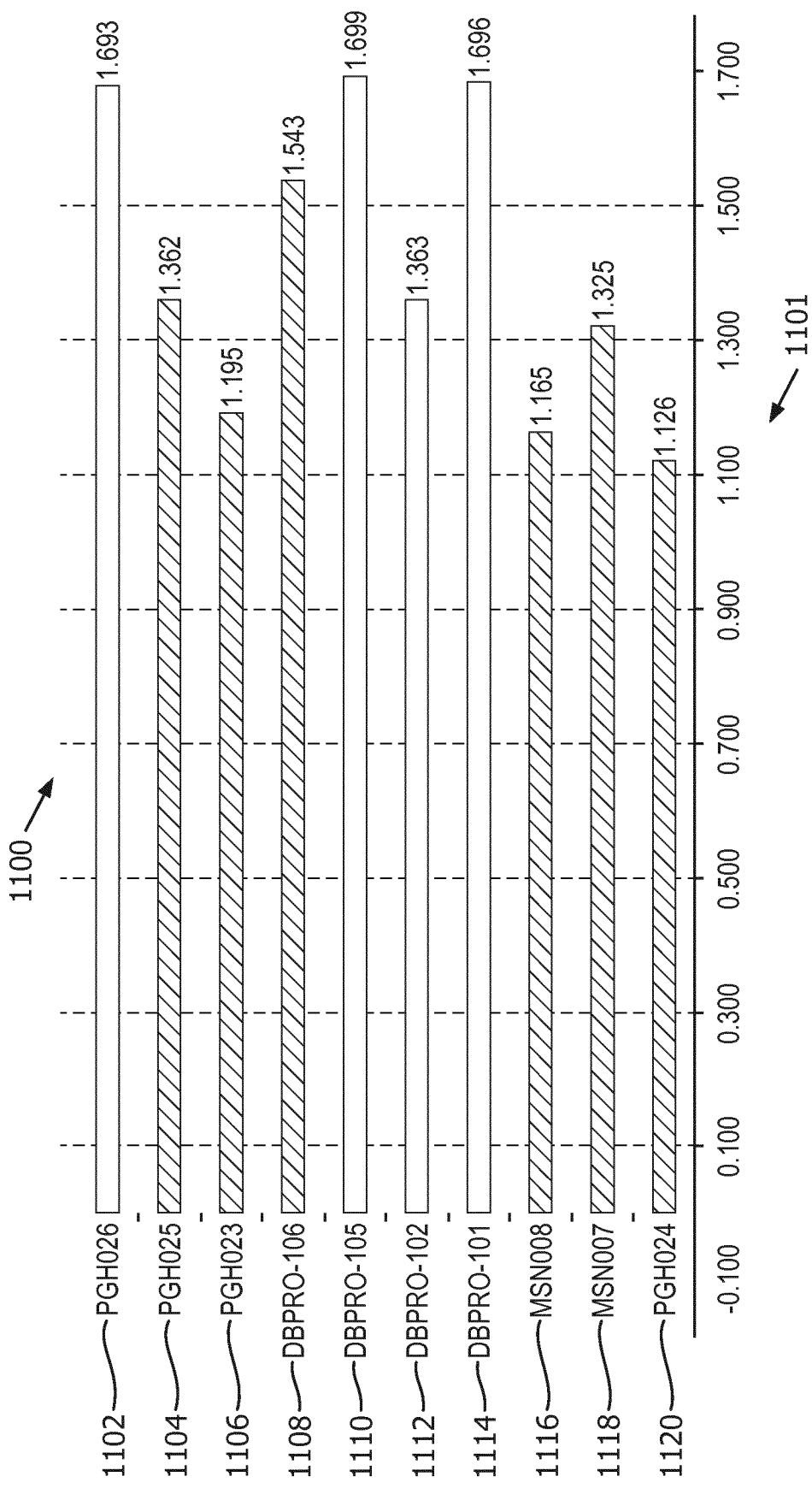
FIG. 11 illustrates experimental alpha power data for ten subjects generated by the system.

FIG. 11 illustrates experimental alpha power data 1100 for 10 subjects (1102-1120) generated by system 10 (FIG. 1). The level of alpha power 1101 in deep sleep was analyzed (e.g., by disturbance determination component 34 shown in FIG. 1 and/or other component of system 10) for several sleep sessions for subjects 1102-1120. In FIG. 11, sensitive subjects 1102, 1110, 1112, and 1114 were identified based on a threshold of 1.3 (this is not intended to be limiting) on the alpha power. In this example, using a threshold of 1.3 on the alpha level power in deep sleep resulted in 100% sensitivity, but 50% specificity (e.g., 3 out of 6 non-sensitive subjects have relative high alpha in deep sleep). Other threshold levels (e.g., threshold levels that facilitate 100% sensitivity and a higher level of specificity) on alpha power are contemplated. In addition, threshold levels for other frequency bands (e.g., the spindle 11-16 Hz band) are contemplated. For example, the spindle 11-16 Hz band and/or other bands may be used because they are indicative of sleep disturbance caused by auditory stimulation. Advantageously, in this embodiment as described above, no stimulation need be provided to the subjects (e.g., subject 12 shown in FIG. 1) during sleep sessions. In some embodiments, stimulator 16 (FIG. 1) is controlled by control component 30 (FIG. 1) to provide the low intensity stimulation, the high intensity stimulation, and no stimulation at different times (e.g., during different sleep cycles) during the same reference sleep session.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. For example, electronic storage 22 may store the thresholds described herein, the algorithms used to determine whether subject 12 is likely to be disturbed by therapy levels of stimulation provided to the subject during sleep sessions, and/or other information. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG, threshold levels, and/or other information may be displayed to subject 12 and/or other users (e.g., doctors, nurses, caregivers, family members, researchers, etc.) via user interface 24. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices.

In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10. In some embodiments, as described below, user interface 24 may be included with sensor 18, stimulator 16, processor 20, electronic storage 22 and/or other components of system 10 in a singular device. In some embodiments, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 includes sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 26 may be provided by resources included in system 10. External resources 26 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, these components may be integrated in to a headset and/or other garments worn by subject 12 during sleep.

Figure 12:
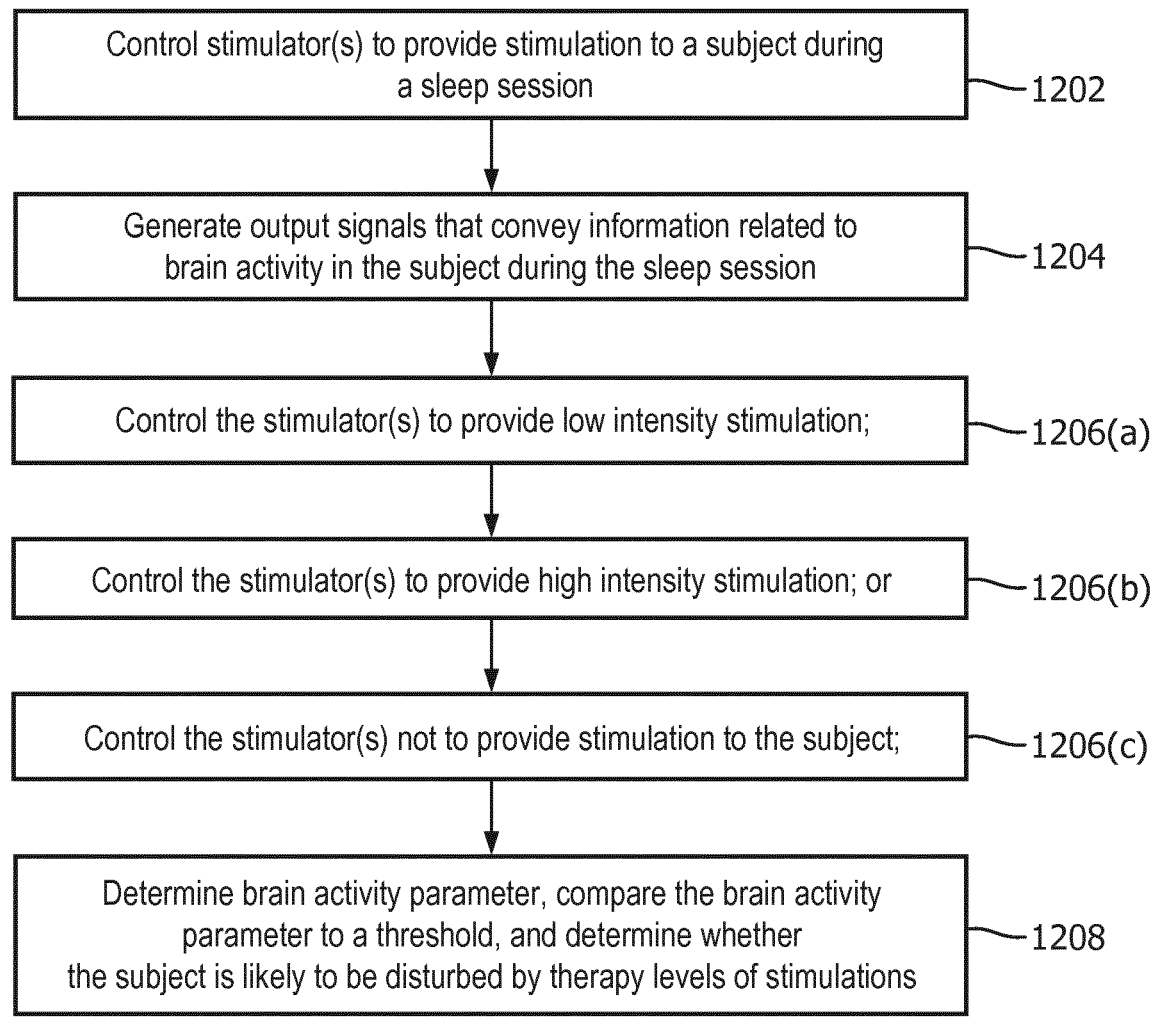
FIG. 12 illustrates a method for determining, with a determination system, whether a subject is likely to be disturbed by therapy levels of stimulation provided to the subject during sleep sessions.

FIG. 12 illustrates a method 1200 for determining, with a determination system, whether a subject is likely to be disturbed by therapy levels of stimulation provided to the subject during sleep sessions. The determination system comprises one or more stimulators, one or more sensors, one or more hardware processors, and/or other components. The one or more hardware processors are configured to execute computer program components. The computer program components comprise a control component, a parameter component, a disturbance determination component, and/or other components. The operations of method 1200 presented below are intended to be illustrative. In some embodiments, method 1200 may be accomplished with one or more additional operations not described, and/or without one or more of the operations discussed. Additionally, the order in which the operations of method 1200 are illustrated in FIG. 12 and described below is not intended to be limiting.

In some embodiments, method 1200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1200 in response to instructions stored electronically on an electronic storage medium. The one or more processing devices may include one or more devices configured through hardware, firmware, and/or software to be specifically designed for execution of one or more of the operations of method 1200.

At an operation 1202, the one or more stimulators are controlled to provide stimulation to a subject during sleep sessions. In some embodiments, the one or more stimulators comprise a tone generator and/or other stimulators. In some embodiments, operation 1202 is performed by a processor component the same as or similar to control component 30 (shown in FIG. 1 and described herein).

At an operation 1204, output signals conveying information related to brain activity in the subject during the sleep sessions are generated. In some embodiments, the one or more sensors comprise electroencephalogram (EEG) sensors and/or other sensors configured to generate EEG output signals conveying information related to brain activity in the subject. In some embodiments, the one or more sensors comprise microphones (for example) and/or other sensors configured to generate output signals conveying information related to the stimulation provided to the subject. In some embodiments, operation 1204 is performed by one or more sensors the same as or similar to sensors 18 (shown in FIG. 1 and described herein).

At an operation 1206, the one or more stimulators are controlled, during a reference sleep session, to provide low intensity stimulation (operation 1206(*a*)), provide high intensity stimulation (operation 1206(*b*)), or not provide any stimulation at all (operation 1206(*c*)) to the subject. In some embodiments, the one or more stimulators are controlled to provide the low intensity stimulation and the high intensity stimulation at different times during the same reference sleep session. The low intensity stimulation comprises stimulation that does not cause sleep disturbances in the subject during the reference sleep session. In some embodiments, the low intensity stimulation comprises tones with a 30-40 decibel volume in up to five tone blocks with a randomized inter tone interval in a 5-30 second range. The high intensity stimulation comprises stimulation that causes sleep disturbances in the subject during the reference sleep session. In some embodiments, operation 1206 is performed by a processor component the same as or similar to control component 30 (shown in FIG. 1 and described herein).

At an operation 1208, a brain activity parameter is determined based on the output signals and/or other information, the brain activity parameter is compared to a threshold that indicates whether the subject is likely to be disturbed by therapy levels of stimulation, and whether the subject is likely to be disturbed by the therapy levels of stimulation is determined based on the comparison. Responsive to the brain activity parameter breaching the brain activity parameter threshold, the subject is determined to be likely to be disturbed by the therapy levels of stimulation.

Responsive to controlling the one or more stimulators to provide the low intensity stimulation, the brain activity parameter comprises a change in an EEG delta power level caused by the low intensity stimulation, and the threshold is a threshold level for the change in the delta power that indicates whether the subject is likely to be disturbed by the therapy levels of stimulation. Responsive to controlling the one or more stimulators to provide the high intensity stimulation, the brain activity parameter comprises a quantity of micro arousals in the subject, and the threshold is a threshold quantity of micro arousals that indicates whether the subject is likely to be disturbed by the therapy levels of stimulation. In some embodiments, the quantity of micro arousals comprises a ratio of a quantity of micro arousals caused by the high intensity stimulation to a quantity of spontaneous micro arousals, and the threshold is a threshold ratio for the micro arousals caused by the high intensity stimulation and the spontaneous arousals. Responsive to controlling the one or more stimulators not to provide stimulation, the brain activity parameter comprises an EEG alpha power level, and the threshold is a threshold level for the alpha power that indicates whether the subject is likely to be disturbed by the therapy levels of stimulation. In some embodiments, operation 1208 is performed by processor components the same as or similar to parameter component 32 and/or disturbance determination component 34 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to determine whether a subject is likely to be disturbed by therapy levels of stimulation provided to the subject during sleep sessions, the system comprising:
    one or more stimulators configured to provide stimulation to the subject during sleep sessions;
    one or more sensors configured to generate output signals conveying information related to brain activity in the subject during the sleep sessions; and
    one or more hardware processors operatively communicating with the one or more stimulators and the one or more sensors, the one or more hardware processors configured by machine-readable instructions to:
    (1) control the one or more stimulators to provide low intensity stimulation to the subject during a reference sleep session, the low intensity stimulation comprising stimulation that does not cause sleep disturbances in the subject during the reference sleep session; or
    (2) control the one or more stimulators to provide high intensity stimulation to the subject during the reference sleep session, the high intensity stimulation comprising stimulation that causes sleep disturbances in the subject during the reference sleep session;
    and
    determine a first brain activity parameter of the subject responsive to the low intensity stimulation being provided based on the output signals during the reference sleep session, determine a second brain activity parameter of the subject responsive to the high intensity stimulation being provided based on the output signals during the reference sleep session, wherein the first brain activity parameter is different than the second brain activity parameter, responsive to determining the first brain activity parameter, compare the first brain activity parameter to a corresponding first brain activity parameter threshold that indicates whether the subject is likely to be disturbed by the therapy levels of stimulation, responsive to determining the second brain activity parameter, compare the second brain activity parameter to a corresponding second brain activity parameter threshold that indicates whether the subject is likely to be disturbed by the therapy levels of stimulation, and responsive to the first brain activity parameter breaching the first brain activity parameter threshold or the second brain activity parameter breaching the second brain activity parameter threshold, determine that the subject is likely to be disturbed by the therapy levels of stimulation.

2. The system of claim 1, wherein the one or more stimulators comprise a tone generator, and the one or more sensors comprise one or more electroencephalogram (EEG) electrodes configured to generate one or more EEG output signals.

3. The system of claim 2, wherein the one or more hardware processors are further configured to control the one or more stimulators to not provide stimulation to the subject during the reference sleep session;
    such that:
    (a) responsive to controlling the one or more stimulators to provide the low intensity stimulation, the first brain activity parameter comprises a change in an EEG delta power level caused by the low intensity stimulation, and the first brain activity parameter threshold is a threshold level for the change in the delta power that indicates whether the subject is likely to be disturbed by the therapy levels of stimulation;
    (b) responsive to controlling the one or more stimulators to provide the high intensity stimulation, the second brain activity parameter comprises a quantity of automatically detected micro arousals in the subject, and the second brain activity parameter threshold is a threshold quantity of micro arousals that indicates whether the subject is likely to be disturbed by the therapy levels of stimulation; or (c) responsive to controlling the one or more stimulators not to provide stimulation, a third brain activity parameter is determined that comprises an EEG alpha power level; and compared to a third brain activity parameter threshold comprising a threshold level for the alpha power during NREM sleep that indicates whether the subject is likely to be disturbed by the therapy levels of stimulation.

4. The system of claim 3, wherein the one or more hardware processors are configured to control the one or more stimulators to provide the low intensity stimulation and the high intensity stimulation at different times during the same reference sleep session.

5. The system of claim 3, wherein the one or more hardware processors are configured such that the quantity of micro arousals comprises a ratio of a quantity of micro arousals caused by the high intensity stimulation to a quantity of spontaneous micro arousals, and the threshold is a threshold ratio for the micro arousals caused by the high intensity stimulation and the spontaneous arousals.

6. The system of claim 1, wherein the one or more stimulators and the one or more hardware processors are configured such that the low intensity stimulation comprises tones with a 30-40 decibel volume in up to five tone blocks with a randomized inter tone interval in a 5-30 second range.

7. A method for determining, with a determination system, whether a subject is likely to be disturbed by therapy levels of stimulation provided to the subject during sleep sessions, the system comprising one or more stimulators, one or more sensors, and one or more hardware processors, the method comprising:
providing, with the one or more stimulators, the stimulation to the subject during the sleep sessions;
generating, with the one or more sensors, output signals conveying information related to brain activity in the subject during the sleep sessions;
(1) controlling, with the one or more processors, the one or more stimulators to provide low intensity stimulation to the subject during a reference sleep session, the low intensity stimulation comprising stimulation that does not cause sleep disturbances in the subject during the reference sleep session; or
(2) controlling, with the one or more processors, the one or more stimulators to provide high intensity stimulation to the subject during the reference sleep session, the high intensity stimulation comprising stimulation that causes sleep disturbances in the subject during the reference sleep session;
and
determining, with the one or more processors, a first brain activity parameter of the subject responsive to the low intensity stimulation being provided based on the output signals during the reference sleep session, determine a second brain activity parameter of the subject responsive to the high intensity stimulation being provided based on the output signals during the reference sleep session, wherein the first brain activity parameter is different than the second brain activity parameter, responsive to determining the first brain activity parameter, comparing the first brain activity parameter to a corresponding first brain activity parameter threshold that indicates whether the subject is likely to be disturbed by the therapy levels of stimulation, responsive to determining the second brain activity parameter, comparing the second brain activity parameter to a corresponding second brain activity parameter threshold that indicates whether the subject is likely to be disturbed by the therapy levels of stimulation, and responsive to the first brain activity parameter breaching the first brain activity parameter threshold or the second brain activity parameter breaching the second brain activity parameter threshold, determining that the subject is likely to be disturbed by the therapy levels of stimulation.

8. The method of claim 7, wherein the one or more stimulators comprise a tone generator, and the one or more sensors comprise one or more electroencephalogram (EEG) electrodes configured to generate one or more EEG output signals.

9. The method of claim 8, further comprising controlling the one or more stimulators to not provide stimulation to the subject during the reference sleep session;
such that:
(a) responsive to controlling the one or more stimulators to provide the low intensity stimulation, the first brain activity parameter comprises a change in an EEG delta power level caused by the low intensity stimulation, and the first brain activity parameter threshold is a threshold level for the change in the delta power that indicates whether the subject is likely to be disturbed by the therapy levels of stimulation;
(b) responsive to controlling the one or more stimulators to provide the high intensity stimulation, the second brain activity parameter comprises a quantity of automatically detected micro arousals in the subject, and the second brain activity parameter threshold is a threshold quantity of micro arousals that indicates whether the subject is likely to be disturbed by the therapy levels of stimulation; or
(c) responsive to controlling the one or more stimulators not to provide stimulation, a third brain activity parameter is determined that comprises an EEG alpha power level and compared to a third brain activity parameter threshold for the alpha power during NREM sleep that indicates whether the subject is likely to be disturbed by the therapy levels of stimulation.

10. The method of claim 9, further comprising controlling the one or more stimulators to provide the low intensity stimulation and the high intensity stimulation at different times during the same reference sleep session.

11. The method of claim 9, wherein the quantity of micro arousals comprises a ratio of a quantity of micro arousals caused by the high intensity stimulation to a quantity of spontaneous micro arousals, and the threshold is a threshold ratio for the micro arousals caused by the high intensity stimulation and the spontaneous arousals.

12. The method of claim 7, wherein the low intensity stimulation comprises tones with a 30-40 decibel volume in up to five tone blocks with a randomized inter tone interval in a 5-30 second range.

13. A system for determining whether a subject is likely to be disturbed by therapy levels of stimulation provided to the subject during sleep sessions, the system comprising:
means for providing the stimulation to the subject during the sleep sessions;
means for generating output signals conveying information related to brain activity in the subject during the sleep sessions;
means for controlling the means for providing to provide low intensity stimulation to the subject during a reference sleep session, the low intensity stimulation comprising stimulation that does not cause sleep disturbances in the subject during the reference sleep session; or means for controlling the means for providing to provide high intensity stimulation to the subject during the reference sleep session, the high intensity stimulation comprising stimulation that causes sleep disturbances in the subject during the reference sleep session;
and
means for determining a first brain activity parameter of the subject responsive to the low intensity stimulation being provided based on the output signals during the reference sleep session, determine a second brain activity parameter of the subject responsive to the high intensity stimulation being provided based on the output signals during the reference sleep session, wherein the first brain activity parameter is different than the second brain activity parameter, responsive to determining the first brain activity parameter, comparing the first brain activity parameter to a corresponding first brain activity parameter threshold that indicates whether the subject is likely to be disturbed by the therapy levels of stimulation, responsive to determining the second brain activity parameter, comparing the second brain activity parameter to a corresponding second brain activity parameter threshold that indicates whether the subject is likely to be disturbed by the therapy levels of stimulation, and responsive to the first brain activity parameter breaching the first brain activity parameter threshold or the second brain activity parameter breaching the second brain activity parameter threshold, determining that the subject is likely to be disturbed by the therapy levels of stimulation.

14. The system of claim 13, wherein the means for providing comprise a tone generator, and the means for generating comprise one or more electroencephalogram (EEG) electrodes configured to generate one or more EEG output signals.

15. The system of claim 14, further comprising means for controlling the means for providing to not provide stimulation to the subject during the reference sleep session; such that:

(a) responsive to controlling the means for providing to provide the low intensity stimulation, the first brain activity parameter comprises a change in an EEG delta power level caused by the low intensity stimulation, and the first brain activity parameter threshold is a threshold level for the change in the delta power that indicates whether the subject is likely to be disturbed by the therapy levels of stimulation;
(b) responsive to controlling the means for providing to provide the high intensity stimulation, the second brain activity parameter comprises a quantity of automatically detected micro arousals in the subject, and the second brain activity parameter threshold is a threshold quantity of micro arousals that indicates whether the subject is likely to be disturbed by the therapy levels of stimulation; or
(c) responsive to controlling the means for providing not to provide stimulation, a third brain activity parameter is determined that comprises an EEG alpha power level and compared to a third brain activity parameter threshold comprising a threshold level for the alpha power during NREM sleep that indicates whether the subject is likely to be disturbed by the therapy levels of stimulation.

16. The system of claim 15, further comprising means for controlling the means for providing to provide the low intensity stimulation and the high intensity stimulation at different times during the same reference sleep session.

17. The system of claim 15, wherein the quantity of micro arousals comprises a ratio of a quantity of micro arousals caused by the high intensity stimulation to a quantity of spontaneous micro arousals, and the threshold is a threshold ratio for the micro arousals caused by the high intensity stimulation and the spontaneous arousals.

18. The system of claim 13, wherein the low intensity stimulation comprises tones with a 30-40 decibel volume in up to five tone blocks with a randomized inter tone interval in a 5-30 second range.

* * * * *